United States Patent
Opara et al.

(10) Patent No.: US 10,398,739 B2
(45) Date of Patent: Sep. 3, 2019

(54) ENCAPSULATED CELLS FOR HORMONE REPLACEMENT THERAPY

(71) Applicant: Wake Forest University Health Sciences, Winston-Salem, NC (US)

(72) Inventors: Emmanuel C. Opara, Durham, NC (US); James J. Yoo, Winston-Salem, NC (US); Justin M. Saul, Oxford, OH (US); Sittadjody Sivanandane, Winston-Salem, NC (US); Anthony Atala, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 14/909,240

(22) PCT Filed: Sep. 2, 2014

(86) PCT No.: PCT/US2014/053705
§ 371 (c)(1),
(2) Date: Feb. 1, 2016

(87) PCT Pub. No.: WO2015/034825
PCT Pub. Date: Mar. 12, 2015

(65) Prior Publication Data
US 2016/0166620 A1 Jun. 16, 2016

Related U.S. Application Data

(60) Provisional application No. 61/872,982, filed on Sep. 3, 2013.

(51) Int. Cl.
| | |
|---|---|
| A61K 35/54 | (2015.01) |
| A61K 47/36 | (2006.01) |
| A61K 9/50 | (2006.01) |
| A61K 35/28 | (2015.01) |
| A61K 31/57 | (2006.01) |
| A61K 31/565 | (2006.01) |

(52) U.S. Cl.
CPC ............ *A61K 35/54* (2013.01); *A61K 9/5036* (2013.01); *A61K 9/5052* (2013.01); *A61K 9/5073* (2013.01); *A61K 31/565* (2013.01); *A61K 31/57* (2013.01); *A61K 35/28* (2013.01); *A61K 47/36* (2013.01)

(58) Field of Classification Search
None
See application file for complete search history.

(56) References Cited

U.S. PATENT DOCUMENTS 6,783,964 B2 * 8/2004 Opara .................. C12N 5/0677
424/423
2006/0084167 A1 4/2006 Cohenford et al.
2014/0127308 A1 5/2014 Opara et al.

FOREIGN PATENT DOCUMENTS

| CN | 101229192 A | 7/2008 | |
|---|---|---|---|
| JP | 2008-228632 | 10/2008 | |
| JP | 2008-275280 | 11/2008 | |
| WO | WO 2006/042132 A2 | 4/2006 | |
| WO | WO 2008/020657 * | 2/2008 | ............... C12N 5/06 |
| WO | WO 2008/098109 A2 | 8/2008 | |
| WO | WO 2012/121874 A1 | 9/2012 | |
| WO | WO 2013/023013 A1 | 2/2013 | |

OTHER PUBLICATIONS

Ng et al., Nature Rev., 16:625-638 (2015).*
Bu et al., Nature, 6(37019:1-14 (2016).*
Ding et al., J. Cancer, 17:1815-1823 (2016).*
Zhang et al., Biomed. Res. Internat., pp. 1-6 (2013).*
Hernandez RM et al. Microcapsules and microcarriers for in situ cell delivery. Advanced Drug Delivery Reviews. Feb. 11, 2010; 62: 711-730.
International Search Report and Written Opinion, PCT/US2014/053705, dated Dec. 24, 2014.
Supplementary European Search Report, EP 14841591.2, dated Mar. 27, 2017.
Extended European Search Report, EP 16179992.9, dated Jan. 13, 2017.
Supplementary European Search Report and Search Opinion, EP 12 75 4353, dated Aug. 7, 2014.
Woodruff TK and Shea LD. The role of the extracellular matrix in ovarian follicle development. Reproductive Sciences. Dec. 1, 2007; 14(8 Suppl): 6-10.
Guo X-X et al. Prevention of osteoporosis in mice after ovariectomy via allograft of microencapsulated ovarian cells. The Anatomical Record. Dec. 2, 2009; 293(2): 200-207.
Lim GJ et al. Cell microencapsulation. Therapeutic Applications of Cell Microencapsulation: Advances in Experimental Medicine and Biology. 2010; 670: 126-136.
Jaffe LA et al. Microinjection of follicle-enclosed mouse oocytes. Methods Mol Biol. 2009; 518: 157-173.
International Search Report and Written Opinion, PCT/US2012/025892, dated May 31, 2012.
Sittadjody S et al. Engineered multilayer ovarian tissue that secretes sex steroids and peptide hormones in response to gonadotropins. Biomaterials. Mar. 2013; 34(10): 2412-2420.
Desai N et al. Evidence of 'genuine empty follicles' in follicular aspirate: a case report. Reproductive Endocrinology. 2009; 24(5): 1171-1175.

(Continued)

*Primary Examiner* — Thomas J. Visone
(74) *Attorney, Agent, or Firm* — Myers Bigel, P.A.

(57) ABSTRACT

A composition comprising microcapsules, the microcapsules containing both live mammalian ovarian granulosa cells and live mammalian ovarian theca cells, is described. In some embodiments, the granulosa cells and the theca cells are contained in separate microcapsules in the composition; in some embodiments, the granulosa cells and the theca cells are contained together in the same microcapsules in the composition. The composition is can be used for estrogen, and optionally also progesterone, delivery, and hence is preferably free or essentially free of oocytes. Methods of using the same and pharmaceutical formulations containing the same are also described.

15 Claims, 9 Drawing Sheets

(56) References Cited

OTHER PUBLICATIONS

Berkholtz CB et al. Extracellular matrix functions in follicle maturation. Semin Reprod Med. Sep. 2006; 24(4): 262-269.
Berkholtz CB et al. Distribution of extracellular matrix proteins type I collagen, type IV collagen, fibronectin, and laminin in mouse folliculogenesis. Histochem Cell Biol. Nov. 2006; 126(5): 583-592.
Hill M. UNSW Embryology, Implantation dynamics. 2010 BGD Practical 3—Implantation. <https://embryology.med.unsw.edu.au/embryology/index.php/2010_BGD_Practical_3_-_Implantation (2016), Accessed ,Nov. 21, 2016.
Kreeger PK et al. The in vitro regulation of ovarian follicle development using alginate-extracellular matrix gels. Biomaterials. Feb. 2006; 27(5): 714-723.
Irving-Rodgers HF et al. Composition and morphology of the follicular basal lamina during atresia of bovine antral follicles. Reproduction. 2002; 123: 97-106.
Irving-Rodgers HF et al. Phenotypes of the ovarian follicular basal lamina predict developmental competence of oocytes. Human Reproduction. 2009; 24(4): 936-944.
Niswender GD et al. Mechanisms controlling the function and life span of the corpus luteum. Physiological Reviews. Jan. 2000; 80(1): 1-29.
Pino, Ana Maria, et al. "Aromatase activity of human mesenchymal stem cells is stimulated by early differentiation vitamin D and leptin", Society for Endocrinology, 191:715-725 (2006).
Takehara, Yuji et al. "The restorative effects of adipose-derived mesenchymal stem cells on damaged ovarian function", Laboratory Investigation, 93:181-193 (2013).

\* cited by examiner

Fig 4: Live/Dead staining of cells in the micro-capsules; Green represents live cells and red represents the dead cells

US 10,398,739 B2

ENCAPSULATED CELLS FOR HORMONE REPLACEMENT THERAPY

RELATED APPLICATIONS

This application is a 35 U.S.C. § 371 national phase entry of PCT Application PCT/US2014/053705, filed Sep. 2, 2014, and published in English on Mar. 12, 2015, as International Publication No. WO 2015/034825, and which claims the benefit of U.S. Provisional Patent Application Ser. No. 61/872,982, filed Sep. 3, 2013, the disclosure of each of which is incorporated by reference herein in its entirety.

FIELD OF THE INVENTION

The present invention concerns compositions and methods for carrying out hormone replacement therapy in subjects in need of such treatment.

BACKGROUND OF THE INVENTION

Estrogens are versatile hormones, which are essential for various physiological functions in women. Reduced estrogen production from the ovaries due to surgical resection, ablative therapy, or menopause leads to various physiological consequences in women. Although hormone replacement therapy is able to compensate for the loss of estrogen production, delivery through pharmacological means results in consistently high serum concentrations. Clinical complications include increased incidence of heart disease and cancer. Accordingly, there is a need for new methods and techniques for delivering estrogen.

SUMMARY OF THE INVENTION

A first aspect of the invention is a composition or pharmaceutical composition comprising, consisting of, or consisting essentially of microcapsules, the microcapsules containing both live mammalian ovarian granulosa cells and live mammalian ovarian theca cells. In some embodiments, the granulosa cells and the theca cells are contained in separate microcapsules in the composition; in some embodiments, the granulosa cells and the theca cells are contained together in the same microcapsules in the composition (e.g., in mixture with one another in the same layer, core, or segment of the microcapsule). The composition is intended primarily for estrogen, and optionally also progesterone, delivery, and hence is preferably free or essentially free of oocytes.

In some embodiments of the invention, live mammalian mesenchymal stem cells are preferably included in the composition, e.g., to enhance the duration of estrogen production by the granulosa cells. The incorporation of mesenchymal cells is neither suggested nor described in our prior application, PCT Application Publication No. WO 2012/121874, the disclosure of which is incorporated by reference herein in its entirety.

In some embodiments, the microcapsules comprise a core and an auxiliary layer surrounding the core, with the core containing the granulosa cells and the auxiliary layer containing the theca cells. In some embodiments, the microcapsules further comprising a first semipermeable layer between the core and the auxiliary layer. In some embodiments, the microcapsules further comprising a second semipermeable layer surrounding the auxiliary layer. In some embodiments, the microcapsules further comprising an external polysaccharide layer surrounding the second semipermeable layer. In some embodiments, the semipermeable layers are formed of a polycation (e.g., a polyamine).

The mesenchymal stem cells are in some embodiments included in the core, mixed together therein with the granulose cells.

In some embodiments, the microcapsules comprise a hydrogel such as a polysaccharide hydrogel (e.g., wherein the core comprises a hydrogel such as a polysaccharide hydrogel, and the surrounding layer comprises a hydrogel such as a polysaccharide hydrogel).

The polysaccharide (e.g. alginate) may be ionically cross-linked. In some embodiments, the ionic cross-linking of the hydrogel is preferably carried out with a strontium salt (e.g., strontium chloride), for example to reduce the calcification of the hydrogel as compared to that which would occur if the cross-linking is carried out with a calcium salt. Again, the use of strontium salt for crosslinking is neither suggested nor described in our prior PCT Application, WO 2012/121874.

A further aspect of the invention is a method of administering estrogen, and optionally also progesterone, to a subject in need thereof, comprising administering the subject a composition as described herein in a treatment-effective amount.

A further aspect of the invention is the use of a composition as described herein for administering estrogen, and optionally also progesterone, to a subject in need thereof, or for the preparation of a medicament for administering estrogen, and optionally also progesterone, to a subject in need thereof.

The present invention is explained in greater detail in the drawings herein and the specification set forth below. The disclosures of all United States patent references cited herein are to be incorporated by reference herein in their entirety.

DETAILED DESCRIPTION OF THE PREFERRED EMBODIMENTS

Figure 1:
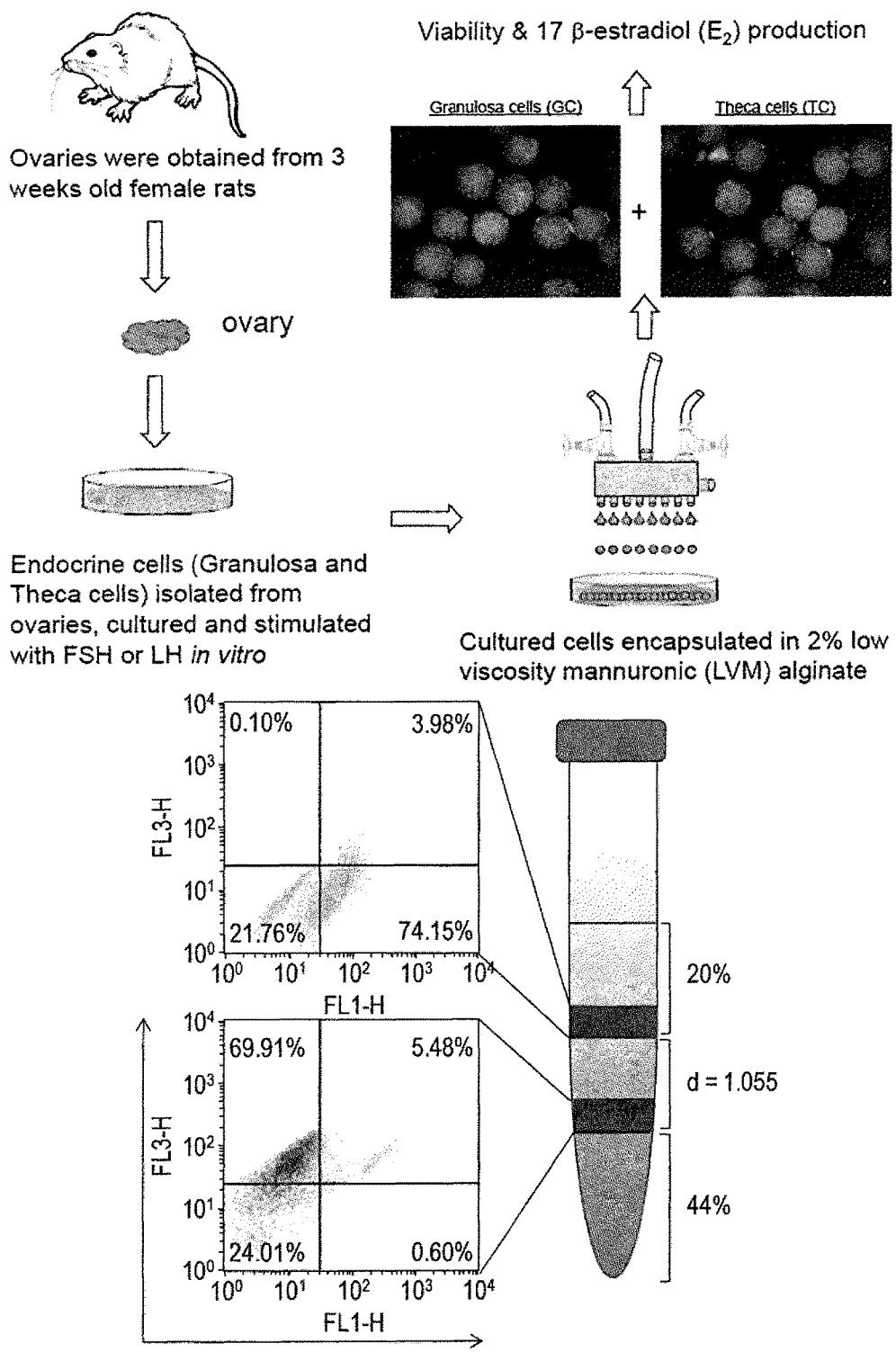
FIG. 1: Schematic representation of encapsulation of ovarian endocrine cells and flow cytometric analysis of purity of isolated granulosa and theca cells purified using a discontinuous percoll gradient.

"Subjects" as used herein are, in general, mammalian subjects. While human subjects are preferred, the subjects may in some embodiments be other animals, such as dogs and cats for veterinary purposes. Subjects are generally female. While the subjects may be of any suitable age, the subjects are typically adults and in some embodiments are menopausal female subjects.

"Treat" as used herein refers to any type of treatment that imparts a benefit to a subject, including but not limited to delaying the onset or reducing the severity of at least one symptom in the subject "Pharmaceutically acceptable" as used herein means that the compound or composition is suitable for administration to a subject to achieve the treatments described herein, without unduly deleterious side effects in light of the severity of the disease and necessity of the treatment.

1. Cells.

Cells used to carry out the present invention are, in general, live mammalian cells collected from a suitable donor. Donors are, in general, mammalian (e.g., human, dog, cat, rabbit, rat, mouse, monkey, chimpanzee, horse, pig, goat, sheep). The donor may be of the same species as the subject being treated, or of a different species. In some embodiments the donor may be the same subject undergoing treatment, where suitable cells were harvested from the subject and stored for subsequent use.

Ovarian cells are isolated from donors and cultured for microcapsule production as desired in accordance with techniques known in the art. See, e.g., Sanjay K. Agarwal et al., *Leptin Antagonizes the Insulin-Like Growth Factor-I Augmentation of Steroidogenesis in Granulosa and Theca Cells of the Human Ovary*, J. Clin Endocrinol Metab 84: 1072-1076 (1999); Jon C. Havelock et al., *Ovarian granulosa cell lines*, Molecular and Cellular Endocrinology 228, 67-78 (2004); Jessica K. Wickenheisser et al., *Human ovarian theca cells in culture*, Trends in Endocrinology & Metabolism 17, 65-71 (2006). In general, fresh tissue is divided by mincing, teasing, comminution and/or collagenase digestion. The desired cells are then isolated from contaminating cells and materials by washing, filtering, centrifuging or picking procedures, and optionally cultured and/or cryopreserved as desired prior to encapsulation.

Mesenchymal stem cells (MSCs) are known and available from a variety of sources. See, e.g. A. Caplan et al., *Mesenchymal stem cells*, J. Orthop Res. 9, 641-50 (1991); see also U.S. Pat. Nos. 8,518,390; 8,076,137; 5,733,542; 7,794,702; 7,101,710; 6,261,549; and 5,197,985. Mesenchymal stem cells may be obtained from commercial sources such as R&D Systems Inc., Minneapolis, Minn., USA).

2. Microcapsule Production.

Encapsulation of live cells can be carried out in accordance with known techniques or variations thereof that will be apparent to those skilled in the art. See, e.g., U.S. Pat. Nos. 6,783,964 and 6,365,385 to Opara, the disclosures of which are incorporated by reference herein in their entirety.

Microcapsules useful in the present invention optionally, but in some embodiments preferably, have at least one semipermeable membrane surrounding a cell-containing interior. The semipermeable membrane permits the diffusion of nutrients, biologically active molecules and other selected products through the surface membrane and into the microcapsule core. The surface membrane contains pores of a size that determines the molecular weight cut-off of the membrane. The membrane pore size is chosen to allow the passage of estrogen, and in some embodiments progesterone, from within the capsule to the external environment, but to exclude the entry of host immune response factors (where the encapsulated cells are not autologous). Such a semipermeable membrane is typically formed from a polycation such as a polyamine (e.g., polylysine and/or polyornithine), as discussed further below.

In one non-limiting example embodiment of an encapsulation technique, U.S. Pat. No. 4,391,909 to Lim et al describes a method in which cells are suspended in sodium alginate in saline, and droplets containing cells are produced. Droplets of cell-containing alginate flow into calcium chloride in saline. The negatively charged alginate droplets bind calcium and form a calcium alginate gel. The microcapsules are washed in saline and incubated with poly-L-lysine or poly-L-ornithine (or combinations thereof); the positively charged poly-1-lysine and/or poly-L-ornithine displaces calcium ions and binds (ionic) negatively charged alginate, producing an outer poly-electrolyte semipermeable membrane. An exterior coating of sodium alginate may be added by washing the microcapsules with a solution of sodium alginate, which ionically bonds to the poly-L-lysine and/or poly-L-ornithine layer (this serves to reduce any inflammatory response that may be provoked in the subject by contact of the polycationic membrane to tissue). This technique produces what has been termed a "single-wall" microcapsule. A "double-wall" microcapsule can be produced by following the same procedure as for single-wall microcapsules, but prior to any incubation with sodium citrate, the microcapsules are again incubated with poly-1-lysine and sodium alginate.

In additional non-limiting examples of encapsulation methods, Chang et al., U.S. Pat. No. 5,084,350 discloses microcapsules enclosed in a larger matrix, where the microcapsules are liquefied once the microcapsules are within the larger matrix. Tsang et al., U.S. Pat. No. 4,663,286 discloses encapsulation using an alginate polymer, where the gel layer is cross-linked with a polycationic polymer such as polylysine, and a second layer formed using a second polycationic polymer (such as polyornithine); the second layer can then be coated by alginate. U.S. Pat. No. 5,762,959 to Soon-Shiong et al. discloses a microcapsule having a solid (non-chelated) alginate gel core of a defined ratio of calcium/barium alginates, with polymer material in the core. U.S. Pat. Nos. 5,801,033 and 5,573,934 to Hubbell et al. describe alginate/polylysine microspheres having a final polymeric coating (e.g., polyethylene glycol (PEG)); Sawhney et al., Biomaterials 13:863 (1991) describe alginate/polylysine microcapsules incorporating a graft copolymer of poly-1-lysine and polyethylene oxide on the microcapsule surface, to improve biocompatibility; U.S. Pat. No. 5,380,536 describes microcapsules with an outermost layer of water soluble non-ionic polymers such as polyethylene(oxide). U.S. Pat. No. 5,227,298 to Weber et al. describes a method for providing a second alginate gel coating to cells already coated with polylysine alginate; both alginate coatings are stabilized with polylysine. U.S. Pat. No. 5,578,314 to Weber et al. provides a method for microencapsulation using multiple coatings of purified alginate. U.S. Pat. No. 5,693,514 to Dorian et al. reports the use of a non-fibrogenic alginate, where the outer surface of the alginate coating is reacted with alkaline earth metal cations comprising calcium ions and/or magnesium ions, to form an alkaline earth metal alginate coating. The outer surface of the alginate coating is not reacted with polylysine. U.S. Pat. No. 5,846,530 to Soon-Shiong describes microcapsules containing cells that have been individually coated with polymerizable alginate, or polymerizable polycations such as polylysine, prior to encapsulation.

When desired, the alginate-polylysine microcapsules can be incubated in sodium citrate to solubilize any calcium alginate that has not reacted with poly-1-lysine, i.e., to solubilize the internal core of sodium alginate containing the cells, thus producing a microcapsule with a liquefied cell-containing core portion. See Lim and Sun, *Science* 210:908 (1980). Such microcapsules are referred to herein as having "chelated", "hollow" or "liquid" cores.

When desired, the microcapsules may be treated or incubated with a physiologically acceptable salt such as sodium sulfate or like agents, in order to increase the durability of the microcapsule, while retaining or not unduly damaging the physiological responsiveness of the cells contained in the microcapsules. See, e.g., U.S. Pat. No. 6,783,964 to Opara.

One currently preferred method for the production of microcapsules is described in O. Khanna et al., *Synthesis of multilayered alginate microcapsules for the sustained release of fibroblast growth factor*-1 J. Biomed. Mater. Res. Part A: 95A: 632-640 (2010).

Microcapsules may be of any suitable size, such as from 10, 20 or 30 microns in diameter, up to 1000, 2000, or 5000 microns in diameter. Microcapsules may contain any suitable amount of cell. For example, in some embodiments, the granulosa cells are included in the microcapsules in an amount of from 1,000 or 2,000 cells per microcapsule up to $1\times10^6$, $1\times10^8$, or $1\times10^9$ cells per microcapsule; and the theca cells are included in the microcapsules an amount of from 1,000 or 2,000 cells per microcapsule up to $1\times10^6$, $1\times10^8$, or $1\times10^9$ cells per microcapsule. Mesenchymal stem cells are included in said microcapsules in any amount from 500 or 1000 cells per microcapsule up to $0.5\times10^6$, to $0.5\times10^8$, $0.5\times10^9$, or $1\times10^9$ cells per microcapsule.

Microcapsules of the present invention may be administered after production, refrigerated and/or cryopreserved for subsequent use, and/or cultured for subsequent use, as desired. Microcapsules of the invention may be washed (e.g., in sterile physiological saline solution) prior to formulation and/or administration, as needed depending upon their manner of production.

3. Formulation and Administration.

Microcapsules of the present invention may be administered per se or formulated for administration by any suitable technique, such as by mixing with sterile physiological saline solution. Microcapsules of the present invention may be administered to subjects as a treatment for any condition in which estrogen replacement therapy is used. The microcapsules may be administered by any suitable technique, including but not limited to surgical implantation or injection (either of which may be carried out subcutaneously, intraperitoneally, intramuscularly, or into any other suitable compartment, particularly into the omentum, such as by deposition into a surgically created omental pouch. Dosage of cells administered can be determined in accordance with known techniques or variations thereof that will be apparent to those skilled in the art. For comparison, in the treatment of diabetes, the International Islet Transplant Registry has recommended transplants of at least 6,000 cells per kilogram of recipient body weight, to achieve euglycemia. In the present invention, the number of cells implanted will depend upon the age and condition of the subject, the particular disorder being treated, etc. In some embodiments of the present invention, from 1,000, 2,000 or 3,000 ovarian (theca plus granulosa) cells per kilogram of recipient body weight, up to 20,000, 40,000 or 60,000 ovarian (theca plus granulosa) cells per kilogram recipient body weight, are administered.

Subjects or patients to be treated by the methods of the present invention include subjects afflicted with, or at increased risk of, one or more of osteoporosis, hot flashes, irregular period, vaginal atrophy, vaginal and/or bladder infection, incontinence (e.g., urge incontinence, stress incontinence), fatigue, sleep disturbances, irritability, mood swings, depression, loss of muscle mass, increased fat tissue, thinning and loss of skin elasticity, loss of bone tissue, impaired cognition etc., which may be associated with menopause, hysterectomy, ovarectomy, or other conditions for which estrogen or hormone replacement therapy is employed.

The present invention is explained in greater detail in the following non-limiting Examples.

Example 1

Isolation of Rat Ovaries

As schematically illustrated in FIG. 1, postnatal day 21 Fischer 344 rats were injected with 1.5 mg/0.2 ml of 17β-estradiol (E2) dissolved in sesame oil, subcutaneously for three consecutive days. The rats were euthanized 24 h after the last injection, ovaries were excised and endocrine cells were isolated as described in Example 2:

Example 2

Cell Isolation and Purification

The endocrine cells were isolated from ovaries of E2-primed immature rats according to Li and Hearn (*J. Biochem. Biophys. Methods* 45, 169-181 (2000). Ovaries collected in ice cold medium 199 (M199) containing HEPES (25 mM), 1 mg/ml bovine serum albumin (BSA), L-glutamine (2 mM), penicillin (10,000 IU/ml), streptomycin (10, 000 μg/ml), and amphotericin B (25 μg/ml). After cleaning the extraneous tissues, the ovaries were washed twice with ice cold M199 and then punctured gently with 27G syringe needles in order to release the loosely packed granulosa from the follicles; cells thus collected were kept on ice. The remaining ovaries were chopped into fine pieces of ~0.25 mm$^2$ and the cells released during this process were collected and kept on ice separately. The pieces of ovaries were then incubated with collagenase (2 mg/ml) and DNase (10 μg/ml) in M199 for 90 min with occasional mixing. The enzyme-digested pieces were dispersed using a Pasteur pipette to obtain a single cell suspension and collected and stored on ice as a separate fraction. Cells from different fractions collected above were purified as per Magoffin and Erickson (*Endocrinology* 122, 2345-2347 (1988)). Briefly, the cells were loaded on top of a discontinuous percoll gradient (44% in the bottom, d=1.055 percoll (specific gravity adjusted to 1.055) in the middle and 20% on the top) and centrifuged at 400×g for 20 minutes at 4° C. Cells from the first interphase (between 20% and d=1.055 layers) were recovered as granulosa cells and those from the second interphase (between d=1.055 and 44% layers) were collected as theca cells (See FIG. 1). The viability of the cells was checked using the trypan blue method and was in the 85-95% range. The purity of each cell type was assessed by flow cytometric analysis using cell-specific markers.

Example 3

Cells Analyzed Using Flow Cytometry

A fraction of the cells (5×10$^6$ cells/cell type) purified using the discontinuous percoll gradient was fixed in 3.7% formaldehyde for 15 minutes.

To verify the purity of the cell types isolated from the rat ovaries, the cells were stained with cell-specific markers and quantified by flow cytometry. Cells from different interphases (See FIG. 1) were incubated with primary antibodies. Antibody for CYP19 (mouse anti-CYP19; Abbiotech; cat. 250549) and FITC-conjugated secondary antibody were used to detect the granulosa cells. Antibody for CYP17A1 (goat anti-CYP17A1; Santa Cruz Biotechnology; cat. sc-46085) and PerCP Cy5.5-conjugated donkey anti-goat IgG secondary antibody were used to detect the theca cells. Cells were incubated with the appropriate primary antibody for 1 h. Unbound antibodies were then washed off and the cells were incubated with the appropriate secondary antibody for 1 h. After washing off the unbound secondary antibodies, cells were analyzed using flow cytometry. The flow cytometric analysis revealed that 74.15% of the cells recovered from the first interphase in the percoll gradient stained positive for CYP19 (FIG. 1) and 69.91% of the cells obtained from the second interphase stained for CYP17A1 (FIG. 1). Cells incubated with only secondary antibodies were used as control.

Example 4

Culture of Granulosa and Theca Cells

Purified granulosa and theca cells were separately incubated at 37° C. under an atmosphere of 5% $CO_2$ in humidified air in T175 flasks (Corning, Corning Inc., NY, USA) cultured for 24 h in McCoy's 5A medium supplement with L-glutamine (2 mM), penicillin (10,000 IU/ml), streptomycin (10,000 μg/ml), amphotericin B (25 μg/ml) and 10% FBS. The medium for granulosa cells was replaced with granulosa growth medium (McCoy's 5A with L-glutamine (2 mM), BSA (1 mg/ml), penicillin (10,000 IU/ml), streptomycin (10,000 μg/ml), and amphotericin B (25 μg/ml), 200 ng/ml oFSH, 100 nM E2 and 10 nM IGF-I) and cultured for an additional 72 h. Similarly, the theca cells were grown for another 72 h in theca growth medium (McCoy's 5A medium supplemented with L-glutamine (2 mM), BSA (1 mg/ml), penicillin (10,000 IU/ml), streptomycin (10,000 μg/ml), amphotericin B (25 μg/ml), 100 ng/ml oLH; 10 nM IGF-I).

Example 5

Immuno-Fluorescence Staining

Each cell type was cultured on chamber slides in respective growth medium and screened for the expression of essential cellular components for steroidogenesis. After fixing the cells in 3.7% formaldehyde for 15 minutes, cells were washed with PBS and blocked with PBS with BSA (1%). The monolayer was then incubated with primary antibodies overnight at 4° C. Granulosa cells were incubated with rabbit anti-FSHR (Santa Cruz Biotechnology; cat. no. sc-13935) and mouse anti-CYP19 (Abbiotech; cat, no. 250549). Similarly theca cells were incubated with rabbit anti-LHR (Santa Cruz Biotechnology; cat. no. sc-25828) and goat anti-CYP17A1 (Santa Cruz Biotechnology; cat. no. sc-46085). After overnight incubation with primary antibodies, the slides were washed with PBS and incubated with secondary antibodies for 2 h at 4° C. The unbound secondary antibodies were washed away and the nucleus was counter-stained with DAPI and cover slips were mounted. The images were acquired using a fluorescence microscope and composite images were made with the help of Image-Pro plus software version 6.3.1.542.

Figure 2:
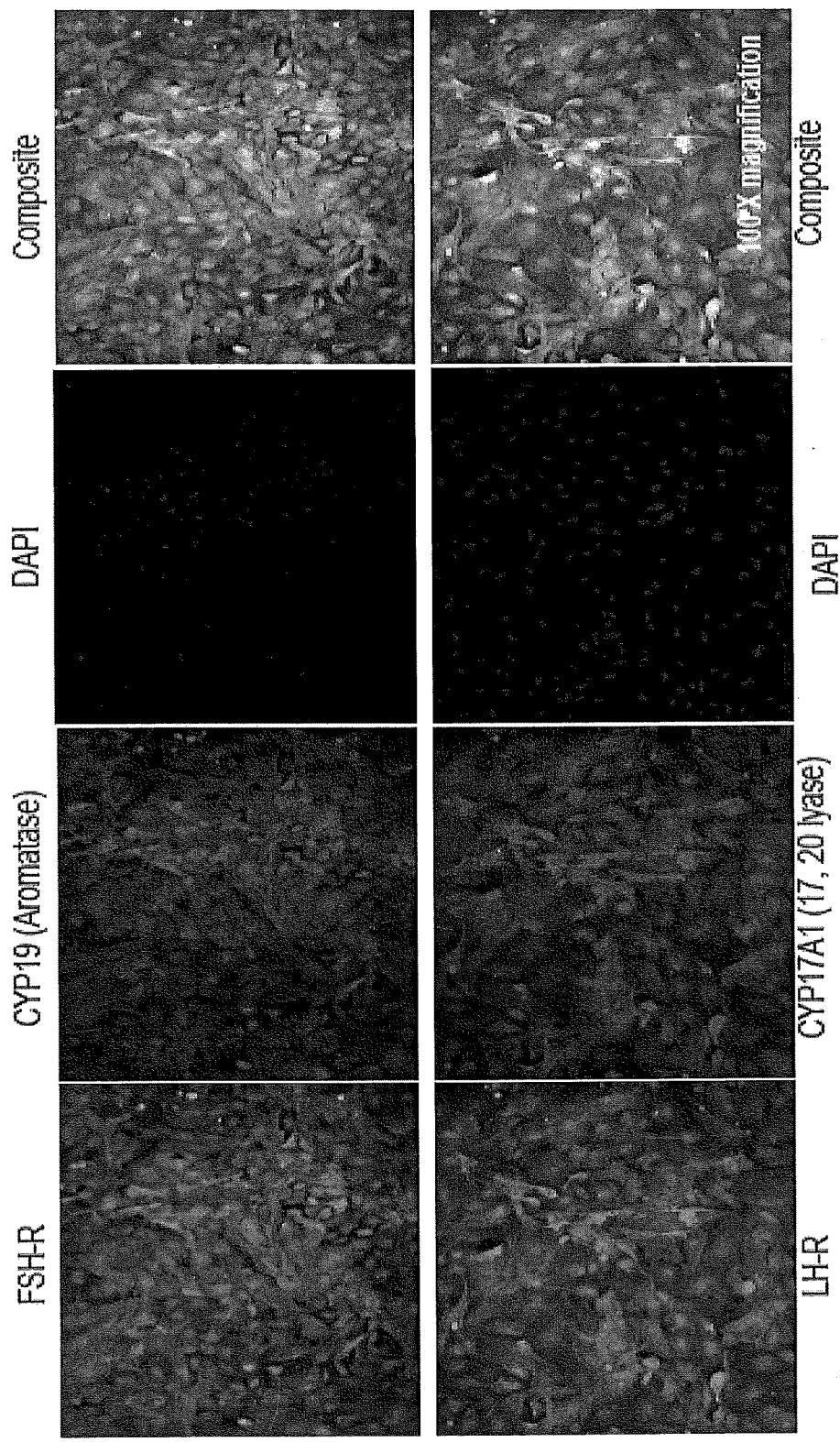
FIG. 2: Immuno-fluorescent staining for FSH-R & CYP19 (aromatase) in granulosa cells (top panel) and for LH-R & CYP17A1 (17, 20 lyase) in theca cells (bottom panel).

While theca cells stained positive for LH-receptor (LHR) and CYP17A1 (FIG. 2), granulosa cells showed positive for FSH-receptor (FSHR) and CYP19 (FIG. 2).

Example 6

Granulosa Cells and Theca Cells Encapsulated Separately

Cultured cells were encapsulated separately by extrusion through a multi-nozzle extruder in 1 to 3% (w/v) ultrapure low viscosity high-mannuronic (LVM) alginate solution into calcium chloride solution for 5 to 15 minutes (for cross-linking) to produce microcapsules of approximately 300 to 600 micron diameter. All the encapsulation and washing steps are carried out at room temperature. Granulosa cell-containing microcapsules and theca cell-containing microcapsules were then combined together with one another in equal parts, co-cultured together in separate chambers of culture inserts in 24-well plates in McCoy's 5A medium supplemented with penicillin/streptomycin (100 IU/ml & 100 μg/ml, respectively), amphotericin B (0.25 μg/ml) and fetal bovine serum (10%) at 37° C. and 5% $CO_2$. The viability and 17β-estradiol production as discussed below was evaluated periodically for 30 days.

Figure 3:
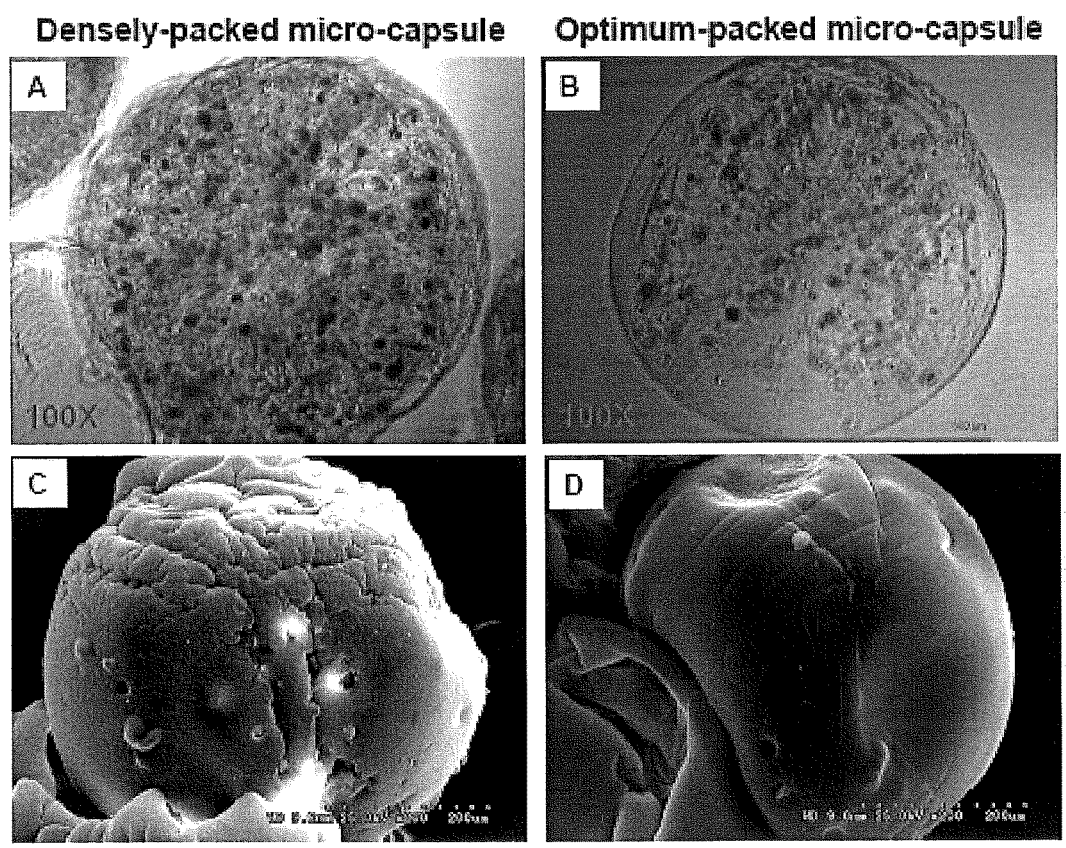
FIG. 3: Phase-contrast microscopy and Scanning electron microscopy images of encapsulated cells in alginate hydrogel microcapsules, showing high packing density of cells (A and C) and low packing density of cells (B and D). This demonstrates the ability to achieve a range of packing densities of cells.

The microcapsules received 50 ng/ml follicle-stimulating hormone (FSH) and 50 ng/ml luteinizing hormone (LH) in long-term cultures. LH treatment increased the expression of CYP17A1 (17, 20 lyase) in theca cells and FSH treatment increased the expression of CYP19 (aromatase) in granulosa cells in vitro (FIG. 2), which improves the steroidogenic potency of these cells. Encapsulation distributed cells evenly in the alginate microcapsules (FIG. 3). It was noted that optimum cell density is an important factor for configuration and structure of the microcapsule, which was approximately 1,000 to 10,000 cells per microcapsule.

Figure 4:
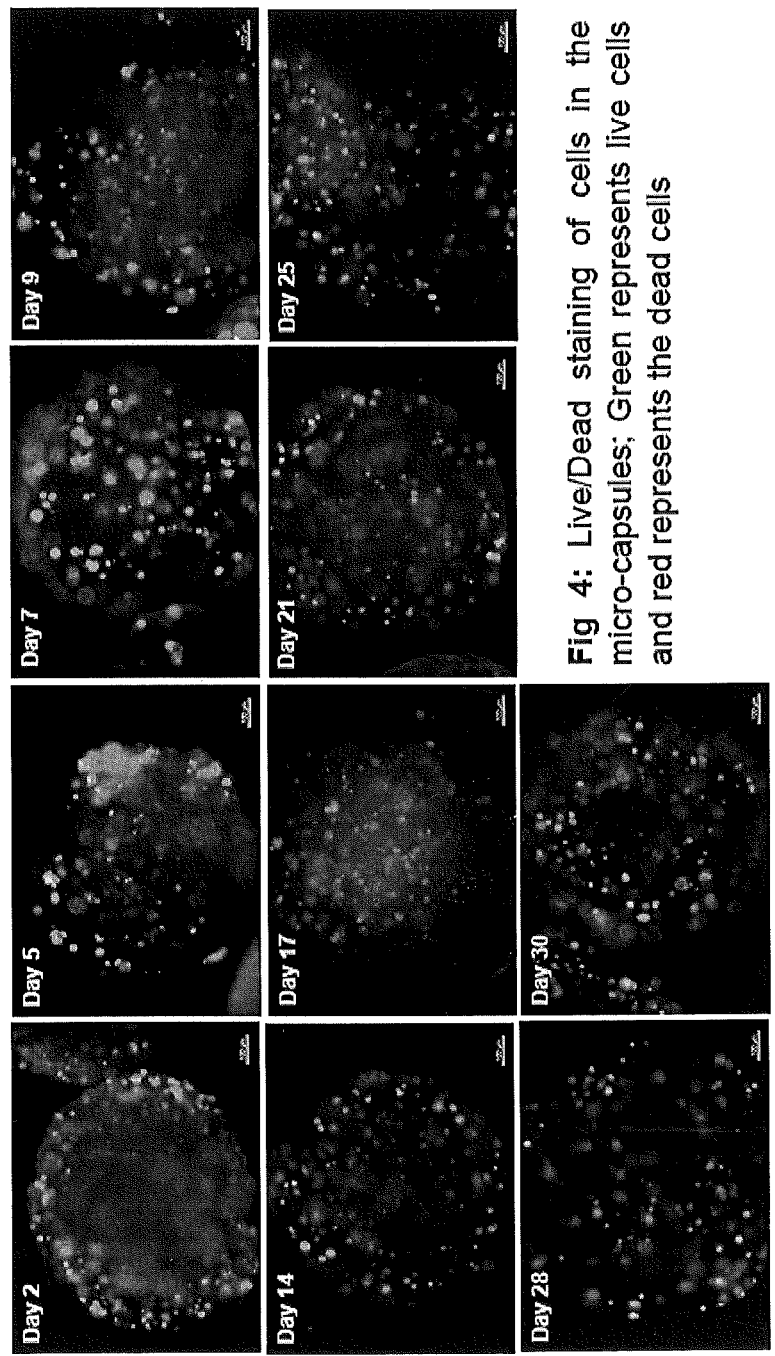
FIG. 4: Live/Dead staining of cells in the micro-capsules; Green represents live cells and red represents the dead cells.

Encapsulated cells had sustained viability during the long-term culture up to day 30 (See Example 10 and FIG. 4). The number of non-viable cells increased in the course of long-term culture.

Figures 5A, 5B, 5C:
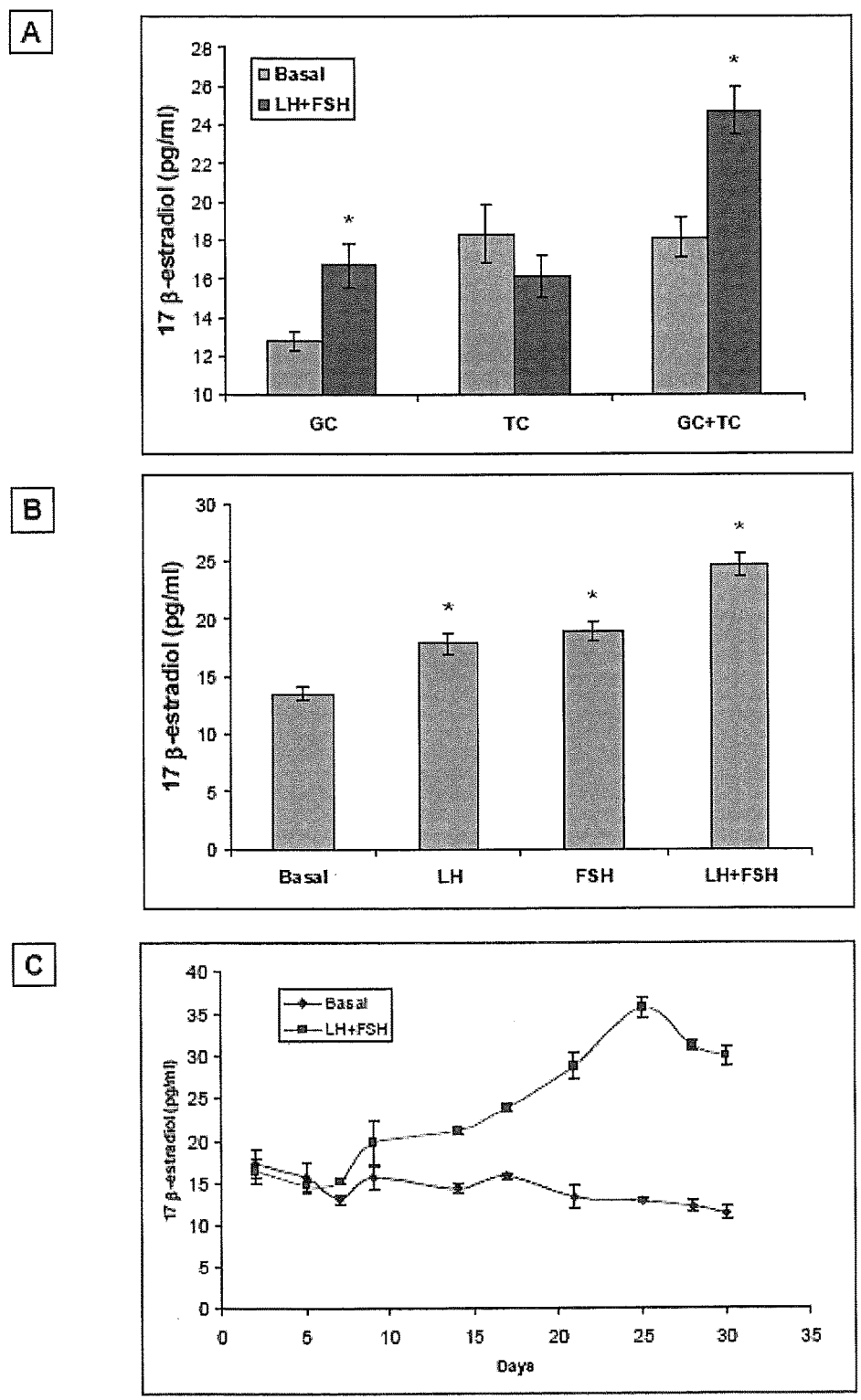
FIGS. 5A to 5C: (A) Granulosa-microcapsules and Theca-microcapsules were cultured separately or co-cultured to see the effect on $E_2$ production. (B) Effect of LH+FSH on $E_2$ production in co-culture system. (C) Sustained $E_2$ production in long-term culture of granulosa cell microcapsule and theca cell microcapsule. *—denotes significance at $P<0.05$ compared to basal condition.

Note that granulosa cell-containing microcapsules co-cultured with theca cell-containing microcapsules produced significantly higher levels of E2 than either cultured individually (FIG. 5A).

In addition, co-culture of granulosa cell-containing microcapsules with theca cell-containing microcapsules secreted increased levels of E2 in response to FSH and LH in the long-term culture in vitro (FIGS. 5B and C).

These data show that ovarian endocrine cells encapsulated in alginate hydrogel microcapsules showed both long-term survival and bioactivity in vitro. With the encapsulation technique we were able to demonstrate that the endocrine unit of ovaries could be recapitulated ex vivo.

In additional experiments, portions of microcapsules were cultured in the presence of FSH (100 ng/ml) and LH (100 ng/ml) for about 30 days and the culture media were collected every alternate day to test the secretion of sex steroids. The levels of 17β-estradiol and progesterone in the culture media were quantified using ELISA kits. 17β-estradiol in culture media was measured with an ELISA kit from Enzo Life Sciences (cat. No. ADI-901-008). The progesterone levels in cell culture media were measured using the ELISA kit from Enzo Life Sciences (cat. no. ADI-901-011). The levels of 17β-estradiol and progesterone were quantified according to the manufacturer's instructions and corrected for their dilutions.

When granulosa cell-containing microcapsules or theca cell-containing microcapsules were incubated separately, there were no significant increases in the production of 17β-estradiol. In the same experiments, the progesterone levels reached 1.3 and 0.8 ng/ml at days 4 and 6, respectively (See FIGS. 5D and 5E).

Figure 5D:
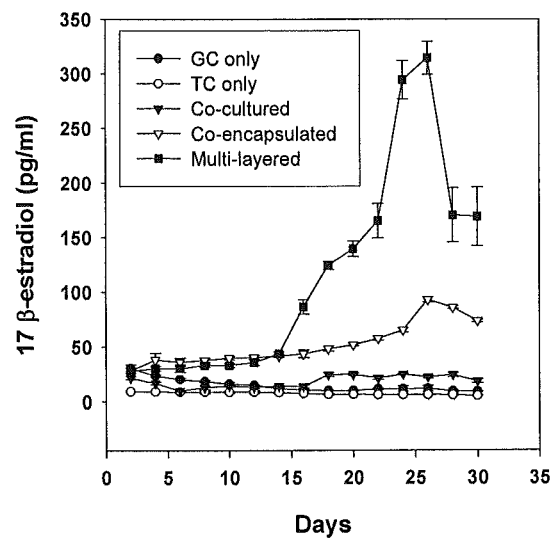
FIG. 5D: When granulosa cell-containing microcapsules or theca cell-containing microcapsules were incubated separately, there were no significant increases in the production of 17β-estradiol. When granulosa cell-containing microcapsules and theca cell-containing microcapsules were co-cultured, the 17β-estradiol level reached ~20 pg/ml at day 18. With co-encapsulated granulosa and theca cells, the 17β-estradiol levels were approximately 5-fold higher by day 25, when compared to basal levels. When granulosa cells and theca cells were encapsulated in two layer microcapsules, there was a ten-fold increase in the 17β-estradiol by day 25.
Figure 5E:
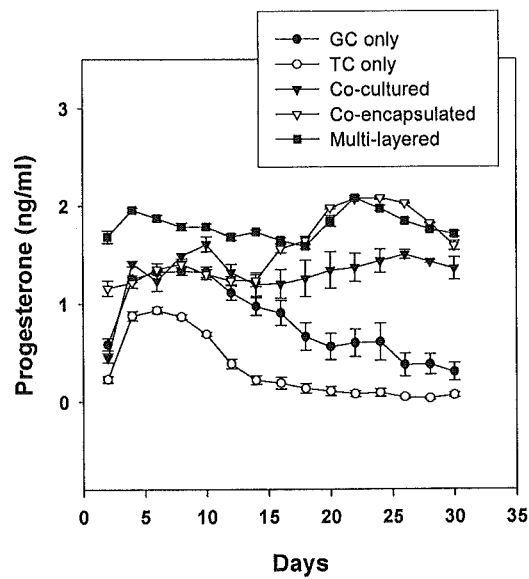
FIG. 5E: When granulosa cell-containing microcapsules or theca cell-containing microcapsules were incubated separately, the progesterone levels reached 1.3 and 0.8 ng/ml at days 4 and 6, respectively. When granulosa cell-containing microcapsules and theca cell-containing microcapsules were co-cultured, the progesterone level peaked at ~1.5 ng/ml at day 26. With co-encapsulated granulosa and theca cells, the progesterone levels were approximately 2 fold higher when compared to basal levels. When granulosa cells and theca cells were encapsulated in two layer microcapsules, progesterone levels were approximately 2 fold higher when compared to basal levels.

When granulosa cell-containing microcapsules and theca cell-containing microcapsules were co-cultured, the 17β-estradiol level reached ~20 pg/ml at day 18 and the progesterone level peaked at ~1.5 ng/ml at day 26 (See FIGS. 5D and 5E).

Example 7

Granulosa Cells and Theca Cells Encapsulated Together

This example is carried out in like manner as Example 6 above, except that the granulosa and theca cells are mixed together in essentially equal amounts prior to extrusion, so that the two are encapsulated together.

A portion of microcapsules were cultured in the presence of FSH (100 ng/ml) and LH (100 ng/ml) for about 30 days and the culture media were collected every alternate day to test the secretion of sex steroids. The levels of 17β-estradiol and progesterone in the culture media were quantified using ELISA kits. 17β-Estradiol in culture media was measured with an ELISA kit from Enzo Life Sciences (cat. No. ADI-901-008). The progesterone levels in cell culture media were measured using the ELISA kit from Enzo Life Sciences (cat. no. ADI-901-011). The levels of 17β-estradiol and progesterone were quantified according to the manufacturer's instructions and corrected for their dilutions. Encapsulated cells responded to the gonadotropins from day 2 onward. The 17β-estradiol levels were approximately 5-fold higher by day 25, when compared to basal levels, and the progesterone levels were approximately 2 fold higher when compared to basal levels; see FIGS. 5D and 5E.

Example 8

Porcine Bone Marrow Stromal Cells Encapsulated Together in Layers

Two layer microcapsules (schematically illustrated in FIG. 6) were produced in accordance with the technique described in O. Khanna et al., *J. Biomed. Mater. Res. Part A* 95A: 632-640 (2010). Briefly, porcine bone marrow stromal cells (pBMSC) were cultured in DMEM supplemented with penicillin/streptomycin (100 IU/ml & 100 μg/ml, respectively), amphotericin 13 (0.25 μg/ml), fetal bovine serum (10%) at 37° C. and 5% $CO_2$ and tagged with vital fluorescent probe CellTracker green and CellTracker orange (invitrogen). pBMSC probed with CellTracker green were encapsulated in 1-2% low viscosity high-mannuronic (LVM) alginate by extrusion through a multi-nozzle extruder into a calcium chloride solution. The microcapsules were then suspended with a 0.05 to 0.2% poly-L-ornithine solution for about 5 to 30 minutes at 4° C. to create the permselective membrane layer. The coated microcapsules were then coated with a second layer of alginate, which was 0.5 to 2% (w/v) low viscosity high-glucoronic alginate (LVG) containing CellTracker orange-probed pBMSC. About 1,000 to 10,000 cells are included in each layer of the capsule.

Example 9

Granulosa Cells and Theca Cells Encapsulated in a Two Layer Microcapsule

Figure 6:
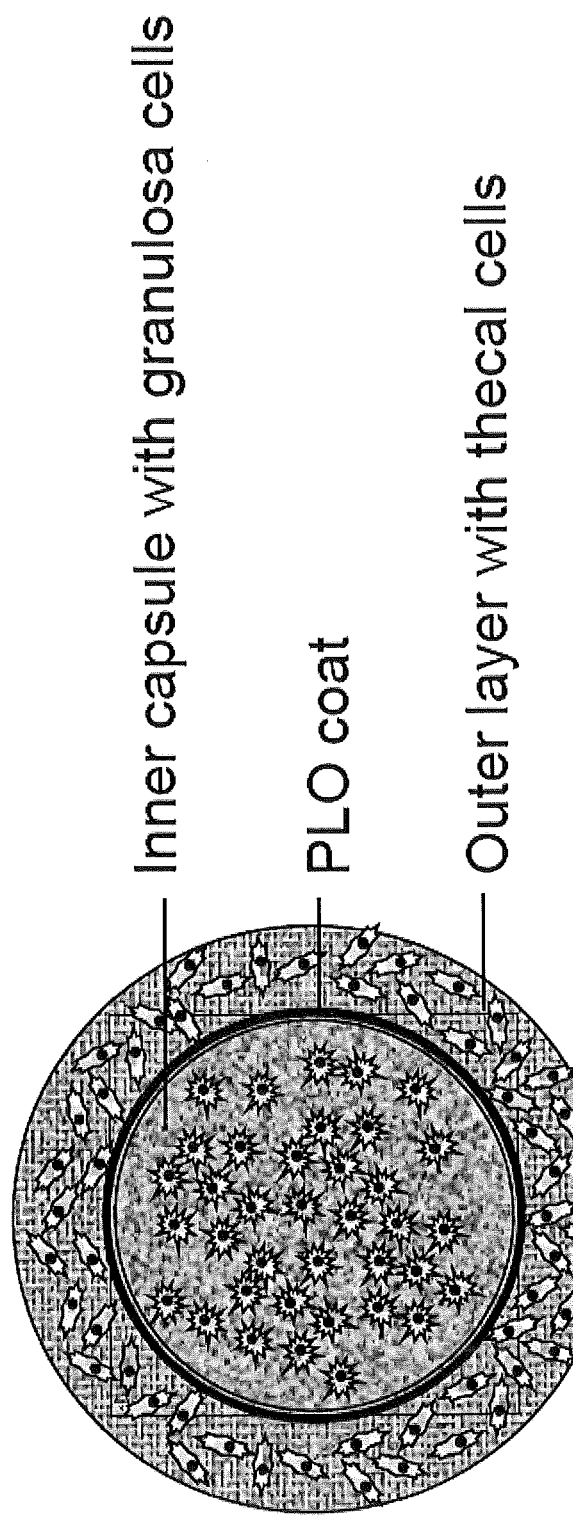
FIG. 6: Schematic diagram of a multi-layer microcapsule.

Granulosa cells were encapsulated in 1.5% (w/v) LVM and coated with poly-L-ornithine (PLO) (0.1% w/v) for 20 minutes. The PLO-coated microcapsules were then mixed with theca cells suspended in 1.5% (w/v) LVM and encapsulated again using the micro-fluidic device (FIG. 1) in order to obtain multi-layered microcapsules, which resemble the structural architecture of native follicles as depicted in FIG. 6 (referred to as multi-layered microcapsules).

A portion of microcapsules were cultured in the presence of FSH (100 ng/ml) and LH (100 ng/ml) for about 30 days and the culture media were collected every alternate day to test the secretion of sex steroids. The levels of 17β-estradiol and progesterone in the culture media were quantified using ELISA kits. 17β-estradiol in culture media was measured with an ELISA kit from Enzo Life Sciences (cat. No. ADI-901-008). The progesterone levels in cell culture media were measured using the ELISA kit from Enzo Life Sciences (cat. no. ADI-901-011). The levels of 17β-estradiol and progesterone were quantified according to the manufacturer's instructions and corrected for their dilutions. There was a ten-fold increase in the 17β-estradiol by day 25 and progesterone levels were approximately 2 fold higher when compared to basal levels, see FIGS. 5D and 5E.

To demonstrate the differential compartmentalization of different cell types in the multi-layered microcapsules, the granulosa cells were pre-stained with Cell Tracker green (Invitrogen, cat. No. C2925) and the theca cells were pre-stained with Cell-tracker Orange (Invitrogen, cat. No. C2927), prior to the synthesis of the multi-layered microcapsules. The multi-layered microcapsules were imaged using a confocal microscope (Zeiss LSM510).

Example 10

Viability of Encapsulated Ovarian Endocrine Cells

The viability of the encapsulate cells were assessed using live dead analysis. A portion of microcapsules from Examples 6, 7, 8, and 9 were cultured in the presence of FSH (100 ng/ml) and LH (100 ng/ml) for about 30 days and the culture media were collected approximately every third day to test the viability of the encapsulated cells. At the designated times, encapsulated cells were transferred to a 24-well plate and incubated with 25 µM CFDA SE (carboxyfluorescein diacetate, succinimidyl ester) (Invitrogen, cat. no. V12883) in serum-free medium for 15 minutes at 37° C. under an atmosphere of 5% $CO_2$ in humidified air. Then the CFDA containing medium was replace with medium containing 10% FBS and incubated again under the above-mentioned conditions for an additional 30 min. The serum-containing medium was then replace with 50 µg/ml of propidium iodide (PI) (Invitrogen, cat. no. V12883) and incubated at room temperature for 2 min and the microcapsules were washed to remove excess PI. The microcapsules were then observed under an inverted fluorescence microscope and imaged. The number of live and dead cells was analyzed from the acquired composite image using Image-Pro plus software version 6.3.1.542.

Note: live cells cleave the ester group of membrane permeable non-fluorescent CFDA and convert it into non-permeable—green fluorescent FDA, which gets trapped inside viable cells. On the other hand, dead cells have a compromised membrane whereby propidium penetrates into the nucleus and stains the DNA red. The periodical live/dead analysis revealed the encapsulated ovarian endocrine cells had a sustained viability throughout the period of long-term culture (See FIG. 4).

Example 11

In Vivo Functions of Tissue-Engineered Ovarian Endocrine Unit

Figure 7A:
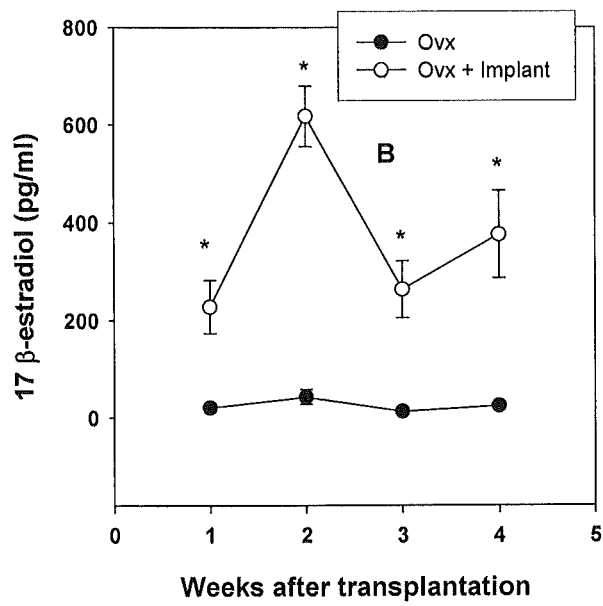
FIGS. 7A and 7B: Sustained E2 and progesterone production by Tissue-construct in vivo. Each data point represents mean±SEM of 6 values.
Figure 7B:
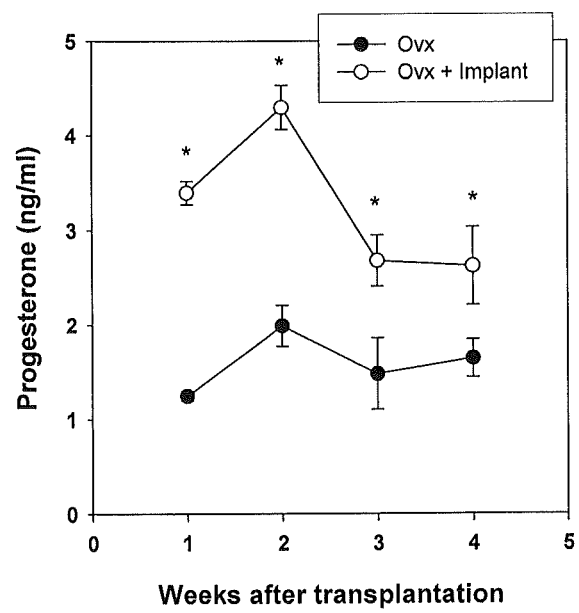

Ovariectomy and implantation of multi-layered microcapsules: Six month old Fisher 344 rats were ovariectomized bilaterally under anaesthesia and their blood levels of $E_2$ and $P_4$ were followed until they reach the basal levels. Once the basal levels were reached the multi-layered microcapsules, from Example 9, were implanted in a pouch made from the great omentum mesentery of the ovx rats. Approximately 1000 microcapsules lodging $0.5 \times 10^6$ cells of each cell type were implanted in each of the experimental rats (n=5). The control rats (n=5) received an equivalent number of blank alginate microcapsules in the omental pouch. The levels of 17β-estradiol and progesterone in the blood plasma were quantified using ELISA kits. 17β-Estradiol in plasma was measured using ELISA kits from Enzo Life Sciences (cat, no. ADI-901-174). The progesterone levels in blood plasma were measured using the ELISA kit (Enzo, Life sciences, cat. no. ADI-901-011). The levels of 17β-estradiol and progesterone were quantified according to the manufacturer's instructions and corrected for their dilutions. Compared to the ovx control rats, the plasma levels of 17β-estradiol in the tissue-construct transplanted rats were significantly higher in all the time points measured (FIG. 7A). Similarly the progesterone levels were also significantly higher than that of the control rats (FIG. 7B).

Student's t-tests were performed for the in vivo study to compare between the means of hormone levels of microcapsule-implanted rats and that of ovx rats.

Example 12

Long-Term Co-Culture in a 2D System

Figure 8A:
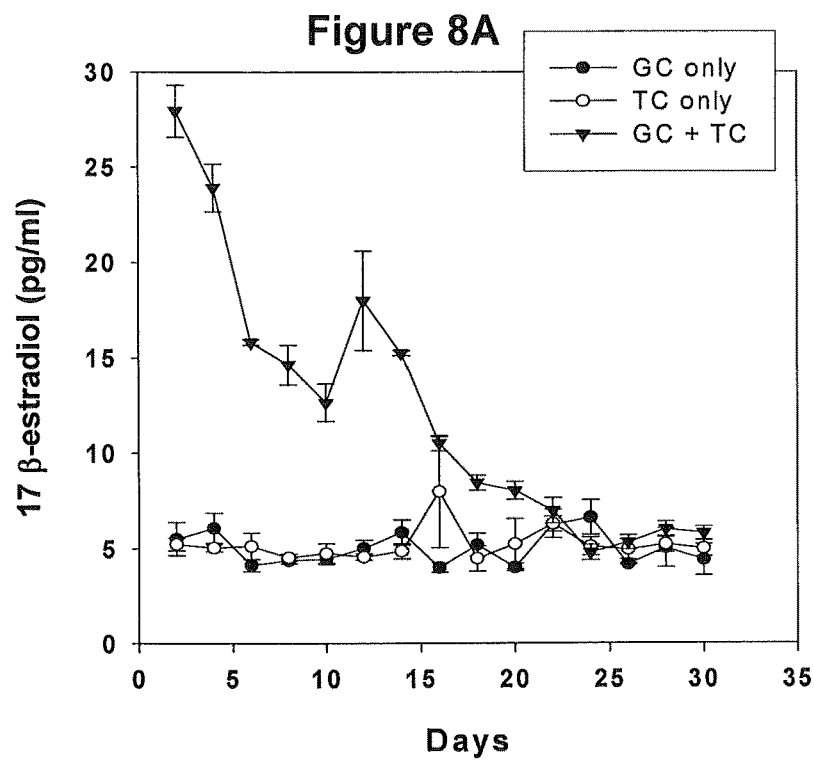
FIGS. 8A and 8B: (A) 17β-estradiol production by co-cultured granulosa cells with theca cells in response to FSH and LH in 2D system. (B) Progesterone production by co-cultured granulosa cells with theca response to FSH and LH in 2D system. Each data point represents mean±SEM of 6 values.
Figure 8B:
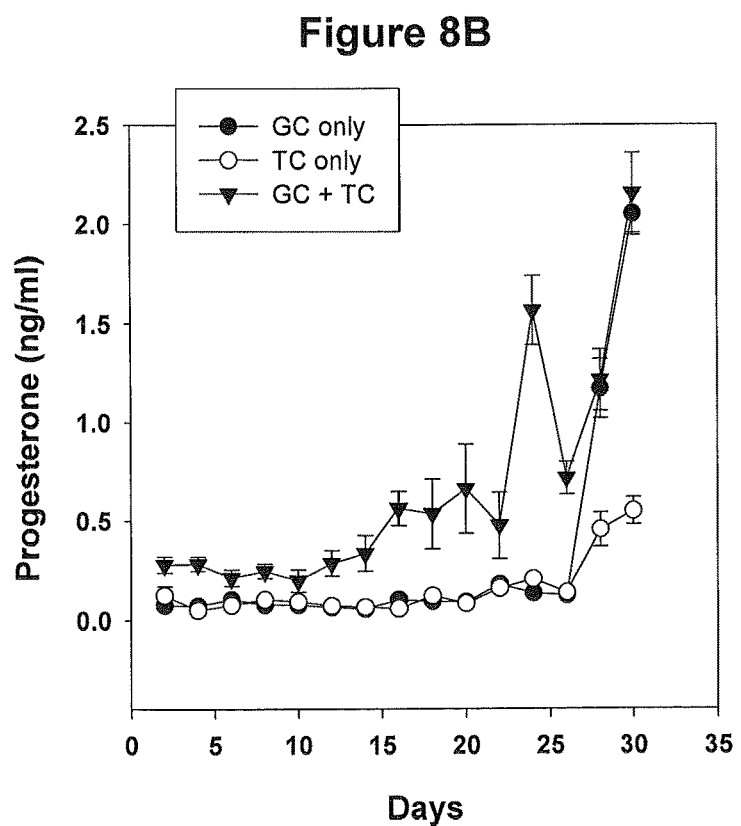

Following isolation, granulosa and theca cells were either cultured separately or co-cultured in a 2D system in the presence of the gonadotrophins, LH and FSH (See FIGS. 8A and 8B). In this example, the levels of progesterone increased with time in the culture media (from 0.2 ng/ml on day 2 to ~2 ng/ml on day 30) while the level of 17β-estradiol decreased from 28 pg/ml on day 2 to ~5 pg/ml on day 30. These data indicate abnormal cell responses in which the granulosa cells lose their estrogenic potential to acquire progesteronic potential thereby enhancing the observed levels of progesterone in the media, in contrast to the normal physiological responses of these cells in the native ovaries.

Example 13

Statistical Analysis

Statistical analyses were performed using SPSS software (version 10.0.1). Results are presented as the mean±S.E.M unless stated otherwise. For the in vitro study, comparisons between the means of hormone levels of three different schemes and the control groups were performed using analysis of variance (ANOVA) followed by post-hoc testing using, when appropriate, Bonferroni correction. Differences were considered to be statistically significant when $P<0.05$.

Example 14

Incorporation of Mesenchymal Stem Cells and Strontium Cross-Linking

We observed decreases in the levels of estrogen production over time both in vitro and in vivo, Without wishing to be bound to any theory of the invention, loss of aromatase activity and calcification of the alginate constructs due to the use of divalent calcium ions ($Ca^{++}$) in the cross-linking process were considered possible reasons for these decreases. We therefore incorporated mesenchymal stem cells (MSCs) into our constructs to enhance levels of aromatase activity and have substituted strontium ions ($Sr^{++}$) for $Ca^{++}$ in the alginate crosslinking step to minimize calcifying effects. As shown in Table 1 (data approximate and error bars not shown), replacement of $Ca^{++}$ with $Sr^{++}$ for crosslinking led to a more stable estrogen secretion profile, while the incorporation of MSCs into our multi-layered constructs led to a significant increase in estrogen secretion. Therefore, the combination of these two modifications ($Sr^{++}$ and the use of MSCs) led to significant increases in estrogen secretion AND elimination of the decline in estrogen secretion at later time points observed in our previous studies,

TABLE 1

17 beta-estradiol secretion from constructs with
and without MSCs, crosslinked with $Sr^{++}$ or $Ca^{++}$,
in picograms per milliliter.[1]

| MSCs | Cation | Day 10 | Day 20 | Day 30 |
|---|---|---|---|---|
| Yes | $Sr^{++}$ | 150 | 210 | 340 |
| Yes | $Ca^{++}$ | 150 | 230 | 230 |
| No | $Sr^{++}$ | 120 | 130 | 130 |
| No | $Ca^{++}$ | 110 | 140 | 120 |

[1]Data generated in in vitro studies using similar culture media and techniques as described in S. Sittadjody et al., *Biomaterials* 34, 2412-2420 (2013).

We note that estrogen secretion from constructs containing MSCs and crosslinked with $Ca^{++}$ peaked at about 380 pg/ml, above that secreted by constructs containing MSCs and crosslinked with $Sr^{++}$, at about day 24, but estrogen secretion from the former declined rapidly thereafter, while estrogen secretion from the latter increased thereafter, as shown by the subsequent data at day 30 in the table above. A similar, but substantially depressed, cross-over pattern was seen for estradiol secretion from constructs that did not contain MSCs.

We also note that the levels of secretion in Table 1 are smaller than in those seen previously due to use of a smaller number of granulosa and theca cells in these more recent studies. However, the addition of MSCs to the construct increased the levels produced by a smaller number of cells to those achieved previously, without the decline in hormone secretion at later times.

The foregoing is illustrative of the present invention, and is not to be construed as limiting thereof. The invention is defined by the following claims, with equivalents of the claims to be included therein.

That which is claimed is:

1. A microcapsule comprising a core and an auxiliary layer surrounding said core, said core containing live mammalian ovarian granulosa cells purified from other ovarian cell types, and said auxiliary layer containing live mammalian ovarian theca cells purified from other ovarian cell types,
    wherein said core and/or said auxiliary layer further contains live mammalian mesenchymal stem cells added to said granulosa cells and/or said theca cells,
    wherein said microcapsule comprises a hydrogel ionically crosslinked with a strontium salt,
    and wherein said microcapsule is free of oocytes.

2. The microcapsule of claim 1, wherein said core further contains said mesenchymal stem cells.

3. The microcapsule of claim 1, said microcapsule further comprising a first semipermeable layer between said core and said auxiliary layer.

4. The microcapsule of claim 1, said microcapsule further comprising a second semipermeable layer surrounding said auxiliary layer.

5. The microcapsule of claim 4, said microcapsule further comprising an external polysaccharide layer surrounding said second semipermeable layer.

6. The microcapsule of claim 4, wherein said semipermeable layers are formed of a polycation.

7. The microcapsule of claim 6, wherein said polycation is a polyamine.

8. The microcapsule of claim 7, wherein said polyamine is poly-L ornithine.

9. The microcapsule of claim 1, wherein said hydrogel comprises a polysaccharide hydrogel.

10. The microcapsule of claim 1, wherein said microcapsule is from 10 microns in diameter, up to 5000 microns in diameter.

11. The microcapsule of claim 1, wherein:
    said granulosa cells are included in said microcapsule in an amount of from 1,000 cells up to $1\times10^9$ cells;
    said theca cells are included in said microcapsule in an amount of from 1,000 cells up to $1\times10^9$ cells; and
    said mesenchymal stem cells are included in said microcapsule in an amount of from 500 cells up to $0.5\times10^9$ or $1\times10^9$ cells.

12. The microcapsule of claim 1, wherein said hydrogel comprises an alginate hydrogel.

13. The microcapsule of claim 1, wherein the strontium salt is strontium chloride.

14. A method of administering estrogen, and optionally also progesterone, to a subject in need thereof, comprising administering to said subject a composition comprising a plurality of the microcapsule according to claim 1 in a treatment-effective amount.

15. The method of claim 14, wherein said administering step is carried out by parenteral injection, or by implantation into the omentum.

* * * * *